United States Patent [19]

Geary et al.

[11] Patent Number: 4,618,442

[45] Date of Patent: Oct. 21, 1986

[54] PLANT CRYOPROTECTION

[76] Inventors: Robert J. Geary; Robert J. Geary, III, both of 6655-53rd St., Vero Beach, Fla. 32960

[21] Appl. No.: 784,935

[22] Filed: Oct. 7, 1985

[51] Int. Cl.$^4$ ................................................ C09K 3/18
[52] U.S. Cl. .......................................... 252/70; 47/2; 252/174.21; 528/419
[58] Field of Search .............. 252/70, 174.21, DIG. 1, 252/DIG. 2; 47/2; 528/419

[56] References Cited

U.S. PATENT DOCUMENTS

| | | | |
|---|---|---|---|
| 2,674,619 | 4/1954 | Lundsted | 252/174.21 |
| 3,048,548 | 8/1962 | Martin et al. | 252/174.21 |
| 3,378,493 | 4/1968 | Jacoby et al. | 252/70 |
| 4,094,805 | 6/1978 | Hansen | 252/70 |
| 4,219,965 | 9/1980 | Freebairn et al. | 47/2 |

FOREIGN PATENT DOCUMENTS

| | | | |
|---|---|---|---|
| 1246488 | 8/1967 | Fed. Rep. of Germany | 252/70 |
| 150379 | 11/1979 | Japan | 252/70 |

OTHER PUBLICATIONS

Ashwood-Smith et al., "Cryoprotection of Mammalian Cells in Tissue Culture with Pluronic Polyols," Cryobiology, 1973, 10 (6), 502-4, (CA 81: 36069).

*Primary Examiner*—Paul Lieberman
*Assistant Examiner*—Robert A. Wax
*Attorney, Agent, or Firm*—Samson B. Leavitt; Michael A. Leavitt

[57] ABSTRACT

Protection of plants against freeze damage by treatment with about 0.05 to about 2.5 wt. % aqueous solution of water soluble nonionic surface active polyoxyethylenated polyoxypropylene block copolymers, optionally also containing urea.

11 Claims, No Drawings

PLANT CRYOPROTECTION

This invention relates to compositions, methods and apparatus for plant cryoprotection, i.e. for increasing the resistance of plants to damage by low, especially freezing, temperatures.

Freezing temperatures have always been a major cause of temporary or permanent damage to plants and plant parts including seedlings, shoots, trunks, bark, growing points, buds, leaves, flowers, fruits and/or vegetables. Numerous types of approaches have been devised for the purpose of inhibiting such plant damage, including laborious, time-consuming and costly development of hardy plant species, mechanical protection such as coating and bagging, and the like. Accepted methods of frost control using wind machines, heaters and/or irrigation involve a high capital cost followed by increasing running costs of rising fuel prices. Treatment, e.g. spraying, of the plant with a suitable cryoprotectant chemical prior to exposure to freezing conditions would appear to constitute a simple and relatively inexpensive solution to this problem. Plant growth inhibitors and other chemicals which delay growth and/or bud development in the spring and thereby avoid injury caused by spring freezes have generally been found to introduce side effects and/or reduce crop yields. Other types of chemicals have been experimented with for plant cryoprotection including polyvinyl pyrrolidone, glycerol, ethylene glycol, and the dodecyl ether of polyethylene glycol (DEPEG). However, as stated in "Analysis and Improvement of Plant Cold Hardness" by Olien and Smith, CRC Press, Inc., Boca Raton, Florida (1981), page 188, "Despite numerous attempts to increase hardiness with chemicals, few if any practical applications have resulted to date . . . The search for chemicals which will increase hardiness continues, however, and may well lead to commercially acceptable methods of reducing field injury."

It is an object of this invention to provide such a chemical. Another object of this invention is the provision of a plant cryoprotectant chemical which will not be subject to one or more of the above disadvantages. Still another object of this invention is the provision of a plant cryoprotectant chemical which is non-phytotoxic, non-toxic, biodegradable and environmentally acceptable. Yet another object of this invention is the provision of compositions, methods and apparatus for employing such chemical for cryoprotection, i.e. increasing the resistance of plants to damage by low, especially freezing, temperatures. Other objects and advantages will appear as the description proceeds.

The attainment of one or more of the above objects is made possible by this invention which includes a method of increasing the resistance of plants to damage by freezing conditions comprising applying to the plant surfaces prior to exposure to such conditions an aqueous solution containing, approximately by weight and as an essential active cryoprotectant component, 0.05% to 2.5% of a water soluble nonionic surface active polyoxyethylenated polyoxypropylene block copolymer having a molecular weight of about 2,000 to about 7,000 and a molar ratio of propylene oxide:ethylene oxide of about 2.5:1 to about 0.7:1.

The invention also includes the provision of the above-defined aqueous solutions and plant spray apparatus containing same, for plant cryoprotectant purposes.

The invention further includes the provision of an aqueous plant cryoprotectant solution in which the solute consists essentially of, approximately by weight, 0.05% to 2.5%, preferably about 0.1 to about 0.5%, more preferably about 0.25%, of a water soluble nonionic surface active polyoxyethylenated polyoxypropylene block copolymer having a molecular weight of about 2,000 to about 7,000, preferably about 4,000 to about 5,000 and a molar ratio of propylene oxide:ethylene oxide (Pr.O.:E.O.) of about 2.5:1 to about 0.7:1, preferably about 1:1, and 0 to 2, preferably about 0.5 to about 2, parts of urea per part of said copolymer, in addition to the method of treating plants therewith and plant spray apparatus containing same.

The above-defined block copolymer is a well known type of nonionic surfactant commonly made by condensing the requisite number of water solubilizing moles of ethylene oxide (E.O.) with a polypropyleneglycol hydrophobe nucleus of requisite molecular weight. These surfactants have good wetting, dispersing, emulsifying, and detergency properties combined with low foam. They have been used as detergent-active agents, and in agriculture for improving wetting properties and for solubilizing, dispersing or emulsifying other functionally active components such as pesticides, growth regulators, fertilizers and the like, i.e. as secondary, assistant or auxiliary agents and not as the sole or major active component. For any given polyoxypropylene hydrophobe, the water solubility of the copolymer varies directly with the percentage of polyoxyethylene combined therewith, i.e. the molar ratio E.O.:Pr.O., or inversely with the molar ratio Pr.O.:E.O. All the copolymers operative herein are water soluble at the defined concentrations at ambient temperatures to yield generally clear solutions, although it will be understood that the terms "water soluble", and "solution" as employed herein include products which are colloidal, or readily water-dispersible or -emulsifiable and the resulting aqueous "solutions" containing them.

The nonionic surfactant copolymers suitable for use in this invention are commercially available. The Monolan products of Diamond Shamrock Corporation, described in its Product Bulletin entitled "Monolan Series", 1982 are representative, ranging from clear liquids to pastes or semi-solids with increasing molecular weight. Preferred among such products are Monolan 2800, a clear liquid with a molecular weight (MW) of about 2800 based on a 1750 MW polyoxypropylene hydrophobe (Pr.O.:E.E. of 1.67:1); and Monolan 6400, a semi-solid of about 5800 MW based on a 3200 MW Pr.O. hydrophobe (Pr.O.:E.O. of 1.22:1). Most preferred is Monolan 4500, a semi-solid of about 4600 MW based on a 2200 MW Pr.O. hydrophobe (Pr.O.:E.O. of about 0.92:1 or about 1:1). Nonionic surfactant copolymers operative herein are also available as Pluronic products of BASF-Wyandotte.

According to a further feature of this invention, it has been found that even better protection against freezing conditions, often with faster absorption by the plant, is attainable when the above-described copolymer solution of this invention further contains some urea, preferably about 0.5 to about 2 parts, more preferably about 1 part, of urea per part by weight of the copolymer. The urea should be substantially pure, preferably crystalline, containing little or no biuret, i.e. less than about 0.5 wt. % of biuret.

The solutions employed according to this invention may be made and supplied to the user in more concentrated form, e.g. from about 5 wt. % up to about 60 wt. % or more aqueous solutions of the copolymer and desirably urea, to be suitably diluted with water prior to application to the plant. If the solution is not to be used promptly following its formation, it should be stored in opaque containers, e.g. amber colored glass or the like, to prevent deterioration by exposure of the copolymer to sunlight. In some instances, as when the copolymer is a paste, gum or other semi-solid, and therefore not as readily or quickly soluble as desired, the copolymer and optional urea may be provided in the form of a concentrate in a water-miscible polyhydric alcohol such as glycerin, propylene glycol, ethylene glycol, polypropylene glycol and/or polyethylene glycol. Such concentrates may contain any desired porportion of the copolymer, such as about 5 to about 60 wt. % or more, preferably about 30 to about 50 wt. %, with optional urea, to be stored in opaque containers and suitably diluted with water prior to use.

It is highly preferred that the copolymer solutions of this invention be devoid of (i.e. any significant amounts of) organic or inorganic fertilizers, pesticides, plant hormones and growth regulators, other polymers and coating materials, and the like since it has been found that they diminish or destroy cyroprotective and other desired and desirable effects and properties of this invention. Further, copolymer concentrations of about 3 wt. % or more have for some unknown reason been found to similarly diminish or eliminate the desired cryoprotective effects. Additionally, it was found that solutions prepared from the above-described concentrates of the copolymer in a water-miscible polyhydric alcohol were substantially more slowly absorbed by the plants than solutions prepared from concentrates devoid of the polyhydric alcohol. Such polyhydric alcohol-containing solutions must therefore be applidd to the plants at a relatively longer lead-time, i.e. at least about 36 hours prior to exposure of the treated plants to freezing conditions. Obviously, solutions which are more quickly absorbed by the plants are to be preferred since they may be applied in emergency situations, e.g. involving brief prior warning of impending freeze-ups.

Although the copolymer solutions of this invention may be applied to the plants immediately prior to exposure to freezing conditions to obtain cryoprotective results, it is preferred for optimal results to apply the solutions at least about 6 hours, preferably at least about 24 hours, prior to such exposure to permit more complete absorption of the solutions. For similar reasons, the treated portions of the plants should not be watered or sprayed with any other liquid medium for at least about 6 hours, preferably at least about 24 hours, following the treatment. Any such inadvertant watering or spraying, or rain, during such initial period of absorption may necessitate repetition of the copolymer treatment of this invention. The cryoprotective effects are retained up to about 30 days or more after treatment with these copolymer solutions, as evidenced by significant reductions in bark and stem splitting, defoliation, foliage burn, fruit damage or drop, yellowing, dessication, and other plant damage and mortality when the treated plants are subjected to freezing conditions.

Any suitable plant spray apparatus suitable for spraying aqueous solutions may be employed. An example of such apparatus is a compressed air atomizer such as the Chromist Spray Unit of Gelman Instrument. The plants to be treated are lightly but thoroughly sprayed, preferably on all their surfaces, short of "run-off". The plants may be in any of their various forms, e.g. seedlings, shrubs, bushes, vines, and trees in any stage of growth, and the application may be made day or night, at ambient warm, room or cold temperatures.

The mechanism by which this invention achieves its desired cryoprotective effects is as yet not fully understood. It functions systemically following absorption of the copolymer solution applied to the plant surfaces. A plant response to the treatment has been recognized which indicates that significant translocation of the copolymer, or a derivative thereof, occurs in the treated plant following such absorption. More particularly, when young growing plants were sprayed with the copolymer solution of this invention and exposed to heavy freeze conditions one month later, the lower leaves which had been originally sprayed sustained significant damage whereas the upper newly grown parts of the plant (which were of course not directly sprayed) were protected from the frost and showed little or no damage. Another plant response to the treatment according to this invention has been noted, namely stimulation of plant growth relative to untreated plants.

The following examples of certain embodiments of this invention are to be regarded as only illustrative and not limitative. All amounts and proportions referred to herein and in the appended claims are by weight, and temperatures are in degrees F., unless otherwise indicated. The PPC 707 employed in the examples corresponds to the above-mentioned Monolan 4500-polyoxypropylene (MW 2200)/polyoxyethylene, MW 4600.

EXAMPLE 1

A. To 100 parts of water (preferably distilled) at room temperature, e.g. 50°–80° F., in a magnetic stirrer are added 2.5 parts of PPC 707 and the mixture stirred to a water-clear solution concentrate. If not to be used immediately, the concentrate is stored in an opaque container, e.g. amber-colored glass vessel, to prevent deterioration by sunlight. For application to plants, the concentrate is extended with tap water to 1,000 parts, i.e. yielding an 0.25% by weight aqueous solution of the active PPC 707, which solution is loaded into a Chromist compressed air atomizer spray apparatus (Gelman Instrument) for spraying on plant surfaces thoroughly but short of run-off.

B. The procedure of preceding paragraph A is repeated, except that 2.5 parts of urea (substantially pure) are initially added with the 2.5 parts of PPC 707 to the magnetic stirrer.

C. The procedure of paragraph A is repeated except that the magnetic stirrer contains 2.5 parts of (a) polypropylene glycol (M.W. 600), or (b) glycerin or (c) Carbowax 60 (polyethylene glycol) instead of 100 parts of water.

In the following examples, the procedure of Example 1A was followed in making the plant cryoprotectant solution and treating the plant surfaces therewith, unless otherwise indicated.

EXAMPLE 2

TEST IN GEORGIA

This test was conducted on Patio and beefsteak tomato plants and pepper plants in a field in Colquitt County, Georgia, initiated in early fall with PPC 707 and two other chemical treatment solutions for comparison. Different sets of plants were sprayed, beginning about a week after planting, about every week from 5 weeks. About 2½ weeks after planting, all plants were fertilized and dusted with 5% Malathion dust. A month after first spraying, all plants were growing well, tomato plants had blossoms and small green tomatoes. Three days after the last spraying, the plants were subjected to heavy frost conditions in a three day period. Nine days after the last spraying, the temperature in the field dropped to 22° F. for several hours overnight.

Plants treated with PPC 707 appeared most resistant, with only a few burned spots on the bottoms of leaves. Most plants survived, with blooms and vegetables in good condition.

Plants treated with Kingfish liquid fertilizer, a hydrolyzed fish protein claimed to have cryoprotectant properties, at the same 0.25% concentration, were least resistant to freezing conditions, being completely burned and eventually dying.

Plants treated with a solution containing 0.25% of each of PPC 707 and Kingfish liquid fertilizer showed intermediate resistance to freezing conditions, most plants being burned and yellow but not dead.

It was noted that the growing plants sprayed with PPC 707 about a month before the heavy freeze showed damage to the lower leaves which had been originally sprayed whereas the upper, newly grown parts of the plants (which had not been sprayed) were resistant to the freeze conditions, indicating systemic transmigration of the cryoprotectant chemical. This test further indicated that the cryoprotectant effect of the PPC 707 treatment lasted for at least about 1½ months.

The following tests were conducted in the vicinity of Vero Beach, Indian River County, Florida.

EXAMPLE 2

Comparative Citrus Test

Seedlings of the Mandarin orange Cleopatra, growing in soilless culture of vermiculite, peat and perlite were exposed to low temperatures of 40° F. to 50° F. night time for a week in midwinter to harden them off so that they were more resistant to freeze damage.

Different sets of the plants were then sprayed in the open with 0.25% solutions of PPC 707 and of the other solutions listed in Table 3 below, following the procedure of Example 1A. Eight days later, early morning temperatures were about 30° F. for 3.5 hours, with sporadic winds of 5 to 15 mph. Nine days after spraying, the plants were subjected to similar winds and heavy freeze conditions, the official weather bureau records for Indian River County showing the following temperatures for the night of the ninth day and the morning of the tenth day.

TABLE 1

| 8 P.M. | 9 P.M. | 10 P.M. | 11 P.M. | 12 P.M. | 1 A.M. |
|---|---|---|---|---|---|
| 30° F. | 29° F. | 28° F. | 28° F. | 28° F. | 26° F. |
| 2 A.M. | 3 A.M. | 4 A.M. | 5 A.M. | 6 A.M. | 7 A.M. |
| 26° F. | 24° F. | 24° F. | 24° F. | 24° F. | 24° F. |

The treated plants were located about 2 miles from the weather recording station in an area about 2° F. colder than those shown in Table 1.

Fifteen days after being exposed to the above conditions, with temperatures about 40° to 50° F., the cryoprotectant antidefoliation effects of the several solutions were evaluated on to following scale.

TABLE 2

| Rating | Plant Symptoms |
|---|---|
| 0 | plant completely dead |
| 1 | severe defoliation |
| 2 | 70% defoliation |
| 3 | 50% defoliation |
| 4 | 30% defoliation |
| 5 | 20% defoliation |
| 6 | 15% defoliation |
| 7 | 10% defoliation |
| 8 | 5% defoliation |
| 9 | 2.5% defoliation |
| 10 | total freeze resistance |

The results of the evaluation were as follows:

TABLE 3

| Chemical | Rating |
|---|---|
| Tween 60-polyoxyethylene (20) sorbitan monostearate | 1 |
| Teric 12A23B-dodecyl ether of polyethylene (23) glycol | 1 |
| Trycol 550 La1 8-dodecyl ether of polyethylene (9) glycol | 1 |
| Trycol La1 45J-hexadecyl ether of polyethylene (6) glycol | 2 |
| PPC 707-Polyoxypropylene (MW2200)/polyoxyethylene, MW 4600 | 9 |
| PPC 708-Polyoxypropylene (MW1750)/polyoxyethylene, MW 2800 | 8 |
| PPC 709-Polyoxypropylene (MW3200)/polyoxyethylene, MW 5800 | 4 |
| Kingfish hydrolyzed fresh protein | 4 |

EXAMPLE 3

Rose Test

In the same area, but only 2 days prior to the period recorded in Table 1 above, 29 large rose plants of each of several varieties from Jackson and Perkins, all budded on Dr. Huey, were sprayed with PPC 707. Similar control plants were not sprayed. Following exposure to the freeze conditions described in Example 2, flower buds of all varieties were affected, but the control plants were severely defoliated in contrast to the sprayed plants which continued to grow well with no foliage burn. Ten days after said freeze conditions, the bark on the control plants split, but not on the sprayed plants.

Tested plant varieties were Tribute, American, Pride, Snowfire, Oregold, Proud Land, Fragrant Cloud, Tropicana, Double Delight and Olympia.

EXAMPLE 4

Vegetable Test

In the same area, but in the evening of the eighth day prior to the period recorded in Table 1 above, large sweet onion plant and Chinese cabbage plants were sprayed with PPC 707 at 50° F. and 29% humidity, and irrigated during the next 3 days. These sprayed plants were not damaged by the freeze conditions described in Example 2.

EXAMPLE 5

Ornamental and Citrus Test

In the same area and on the same day as the above Rose Test of Example 3, Carissa, Iothosporus, lily, springi fern, gardinia, geranium, navel orange, pink grapefruit and scheffelera plants were sprayed with PPC 707. Following exposure to the freeze conditions described in Example 2, only geranium plants and some types of the scheffelera showed injury, but none serious.

All plants continued to grow and 2 young citrus plants broke out with new growth within 9 days of the freeze.

EXAMPLE 6

Citrus Test

In the same area and on the same day as the above Rose Test, pink grapefruit trees 5 feet high, and citrus seedlings of variety Cleopatra and sour orange were sprayed with PPC 707. Similar control plants were not sprayed.

Following exposure to the freeze conditions described in Example 2, tips of leaves on some of the young new growth on the large grapefruit trees, which had been fertilized and were in soft growth condition, showed slight leaf burn. The citrus seedlings were practically unaffected except a few leaf tips apparently from wind burn.

Twenty-one days after the afore-described freeze conditions, another severe freeze occurred for a total of 14 hours, with temperatures down to 22° F., for most of the night.

The tips of some of the young growth on the grapefruit trees were injured, but one week later, the control trees showed severe injury with 50% defoliation and 75% fruit drop, in contrast to the sprayed trees which surprisingly showed less than 10% defoliation and 10% fruit drop with no injury to undropped fruit.

The citrus seedlings survived both freezes without serious injury and continued to grow well.

EXAMPLE 7

Additive Test on Tomatoes

Different sets of tomato plants were sprayed with 0.25% solutions of PPC 707 (Example 1A), PPC 707 with urea (Example 1B), with glycerin (Example 1C(b)), and with Carbowax 60 (Example 1C(c)). The plants were subjected to freeze conditions 18 hours after spraying, with temperatures of 29° F. for four hours. Plants treated with the PPC 707 and PPC 707/urea solutions were unaffected by the freeze, but plants treated with the PPC 707/glycerin and PPC 707/Carbowax 60 solutions were killed, indicating that the glycerin and Carbowax 60 prevented absorption of an effective amount of the PPC 707 during the 18 hour period between spraying and freeze, and that longer prefreeze periods would be necessary.

This test further indicates the sensitivity of the copolymers of this invention to other materials in the spray solutions. As described above, these copolymers are sensitive to salts. Initial tests on beans indicated that inclusion in the spray solution of low dosage of NPK water soluble fertilizer (Miracle Gro, 2 grams per quart) completely nullified the desired cryoprotectant results. This may explain the lack of recognition in the agriculture art of the cryoprotective properties of these copolymers which have hitherto not been employed as sole active functional agents on plants, trees, etc, This invention has been disclosed with respect to preferred embodiments, and it will be understood that various modifications and variations thereof obvious to those skilled in the art are to be included within the spirit and purview of this application and the scope of the appended claims.

What is claimed is:

1. A method of increasing the resistance of plants to damage by freezing conditions comprising applying to the plant surfaces at ambient non-freezing temperatures about 0.25 to about 9 days prior to exposure to such conditions an aqueous solution containing, approximately by weight and as an essential active cryoprotectant component, 0.1% to 2.5% of a water soluble nonionic surface active polyethoxylated polyoxypropylene block copolymer having a molecular weight of about 2,000 to about 7,000 and a molar ratio of propylene oxide:ethylene oxide of about 2.5:1 to about 0.7:1.

2. A method according to claim 1 wherein said solution contains about 0.25 wt. % of said copolymer.

3. A method according to claim 1 wherein said copolymer has a molecular weight of about 4,000 to about 5,000 and said molar ratio is about 1:1.

4. A method according to claim 1 wherein said solution further contains about 0.5 to about 2 parts of urea per part by weight of said copolymer.

5. An aqueous plant cryoprotectant solution containing, approximately by weight and as essential cryoprotectant components, 0.05% to 2.5% of a water soluble nonionic surface active polyethoxylated polyoxypropylene block copolymer having a molecular weight of about 2,000 to about 7,000 and a molar ratio of propylene oxide:ethylene oxide of about 2.5:1 to about 0.7:1 and about 0.5 to about 2 parts of urea per part of said copolymer.

6. A solution according to claim 5 containing about 0.1 to about 0.5 wt. % of said copolymer.

7. A solution according to claim 5 containing about 0.25 wt. % of said copolymer.

8. A solution according to claim 5 wherein said copolymer has a molecular weight of about 4,000 to about 5,000 and said molar ratio is about 1:1.

9. A solution according to claim 8 wherein said copolymer has a molecular weight of about 4,000 to about 5,000 and said molar ratio is about 1:1.

10. A method according to claim 3 wherein said solution contains about 0.25 wt. % of said copolymer.

11. A method according to claim 10 wherein said solution further contains about 0.5 to about 2 parts of urea per part by weight of said copolymer.

* * * * *